US010576292B2

(12) United States Patent
Orinski

(10) Patent No.: US 10,576,292 B2
(45) Date of Patent: *Mar. 3, 2020

(54) SKULL-MOUNTED DEEP BRAIN STIMULATOR

(71) Applicant: Boston Scientific Neuromodulation Corporation, Valencia, CA (US)

(72) Inventor: William G. Orinski, Reno, NV (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/291,846

(22) Filed: Oct. 12, 2016

(65) Prior Publication Data
US 2017/0151438 A1 Jun. 1, 2017

Related U.S. Application Data

(60) Provisional application No. 62/260,626, filed on Nov. 29, 2015.

(51) Int. Cl.
*A61N 1/37* (2006.01)
*A61N 1/378* (2006.01)
(Continued)

(52) U.S. Cl.
CPC ......... *A61N 1/3752* (2013.01); *A61N 1/3606* (2013.01); *A61N 1/3754* (2013.01); *A61N 1/3787* (2013.01); *A61N 1/37223* (2013.01)

(58) Field of Classification Search
CPC . A61N 1/36; A61N 1/375; A61N 1/05; A61N 1/378; A61N 1/372; A61N 1/3787;
(Continued)

(56) References Cited

U.S. PATENT DOCUMENTS 4,495,917 A 1/1985 Byers
6,272,382 B1 8/2001 Faltys et al.
(Continued)

FOREIGN PATENT DOCUMENTS

WO 2012/138782 10/2012
WO 2013/048396 A1 4/2013

OTHER PUBLICATIONS

International Search Report and Written Opinion regarding corresponding PCT Application No. PCT/US2016/056836, dated Jan. 23, 2017.

(Continued)

*Primary Examiner* — Carl H Layno
*Assistant Examiner* — Jon Eric C Morales
(74) *Attorney, Agent, or Firm* — Lewis & Reese, PLLC

(57) ABSTRACT

An Implantable Pulse Generator (IPG) operable as a Deep Brain Stimulator (DBS) is disclosed which is mountable to the skull of a DBS patient, and which therefore is much closer to the site of intended therapy. The IPG includes an electronics section, a charging coil section, a connector block section configured to connect to the proximal end of implanted leads, and an electrode wire section connecting the connector block section to the electronics section. The electronic section includes a housing that is positionable into a hole formed in the patient's skull. Once so positioned, the housing may be affixed to the skull via bone screws. The charging coil section may be separate from and non-overlapping with the electronics section, or the charging coil section may encircle the electronics section.

16 Claims, 13 Drawing Sheets

(51) Int. Cl.
    *A61N 1/375*     (2006.01)
    *A61N 1/36*     (2006.01)
    *A61N 1/372*     (2006.01)

(58) Field of Classification Search
    CPC ............ A61N 1/36125; A61N 1/37223; A61N 1/37241; A61N 1/3758; A61N 1/36062
    USPC .......................................... 607/45, 129, 139
    See application file for complete search history.

(56) References Cited

U.S. PATENT DOCUMENTS

| | | | |
|---|---|---|---|
| 6,516,227 | B1 | 2/2003 | Meadows et al. |
| 7,263,401 | B2 | 8/2007 | Scott et al. |
| 7,444,181 | B2 | 10/2008 | Shi et al. |
| 8,024,049 | B1 * | 9/2011 | Gilson ................. A61N 1/0534 607/116 |
| 8,335,569 | B2 | 12/2012 | Aghassian |
| 8,457,744 | B2 | 6/2013 | Janzig et al. |
| 8,498,716 | B2 | 7/2013 | Chen et al. |
| 8,538,545 | B2 | 9/2013 | Meskens |
| 8,606,362 | B2 | 12/2013 | He et al. |
| 8,620,436 | B2 | 12/2013 | Parramon et al. |
| 8,694,120 | B2 | 4/2014 | Murtonen |
| 8,768,453 | B2 | 7/2014 | Parramon et al. |
| 8,862,235 | B1 | 10/2014 | Stover et al. |
| 9,398,901 | B2 * | 7/2016 | Tischendorf ....... A61N 1/36139 |
| 2002/0052610 | A1 * | 5/2002 | Skakoon ............. A61N 1/0534 606/129 |
| 2004/0147974 | A1 | 7/2004 | Engmark et al. |
| 2005/0004618 | A1 * | 1/2005 | Scott ...................... A61N 1/375 607/45 |
| 2007/0255338 | A1 * | 11/2007 | Wahlstrand ........ A61N 1/36082 607/45 |
| 2010/0312193 | A1 * | 12/2010 | Stratton et al. ....... A61M 39/02 604/175 |
| 2012/0221074 | A1 * | 8/2012 | Funderburk ......... A61N 1/3752 607/45 |
| 2012/0283800 | A1 | 11/2012 | Perryman et al. |
| 2013/0066400 | A1 | 3/2013 | Perryman et al. |
| 2013/0079849 | A1 | 3/2013 | Perryman et al. |
| 2013/0184794 | A1 | 7/2013 | Feldman et al. |
| 2013/0310901 | A1 | 11/2013 | Perryman et al. |
| 2014/0058480 | A1 | 2/2014 | Perryman et al. |
| 2014/0358194 | A1 | 12/2014 | Vansickle et al. |
| 2015/0066114 | A1 | 3/2015 | Bunyan et al. |
| 2015/0080982 | A1 | 3/2015 | Van Funderburk |
| 2015/0088226 | A1 | 3/2015 | Tourrel et al. |
| 2015/0251011 | A1 | 9/2015 | Ranpura et al. |
| 2015/0360038 | A1 | 12/2015 | Zottola et al. |
| 2016/0066803 | A1 * | 3/2016 | Hu ........................ A61B 90/11 600/561 |
| 2016/0144166 | A1 * | 5/2016 | Decre .................. A61N 1/0534 600/377 |
| 2017/0151440 | A1 * | 6/2017 | Parramon ............ A61N 1/3787 |

OTHER PUBLICATIONS

U.S. Appl. No. 15/090,367, filed Apr. 4, 2015, Parramon.
U.S. Appl. No. 62/260,626, filed Nov. 29, 2015, Orinski.

* cited by examiner

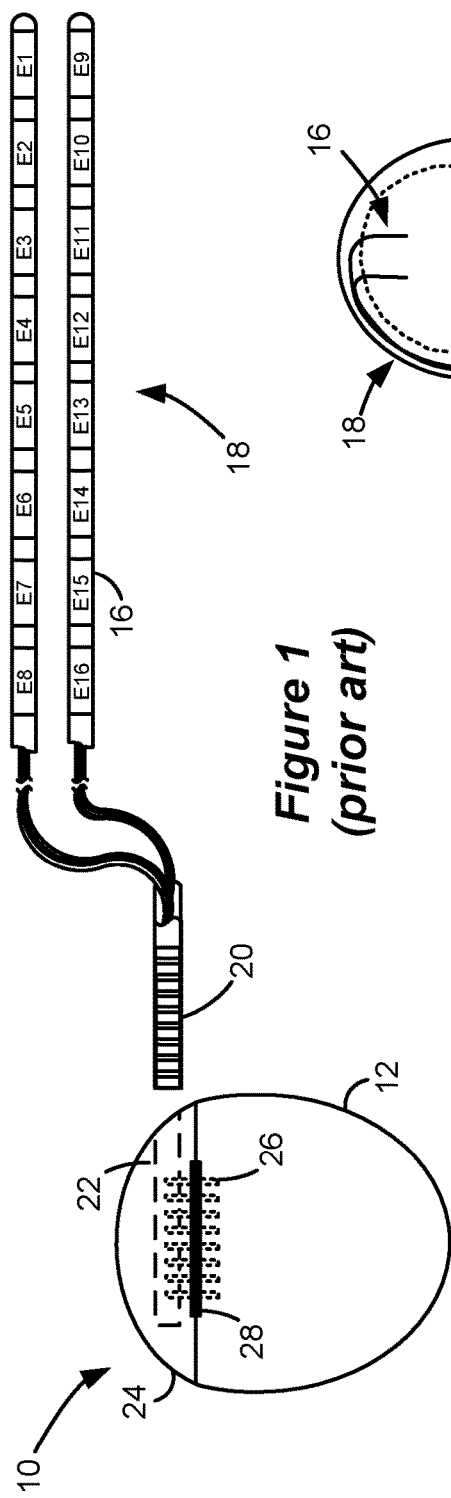
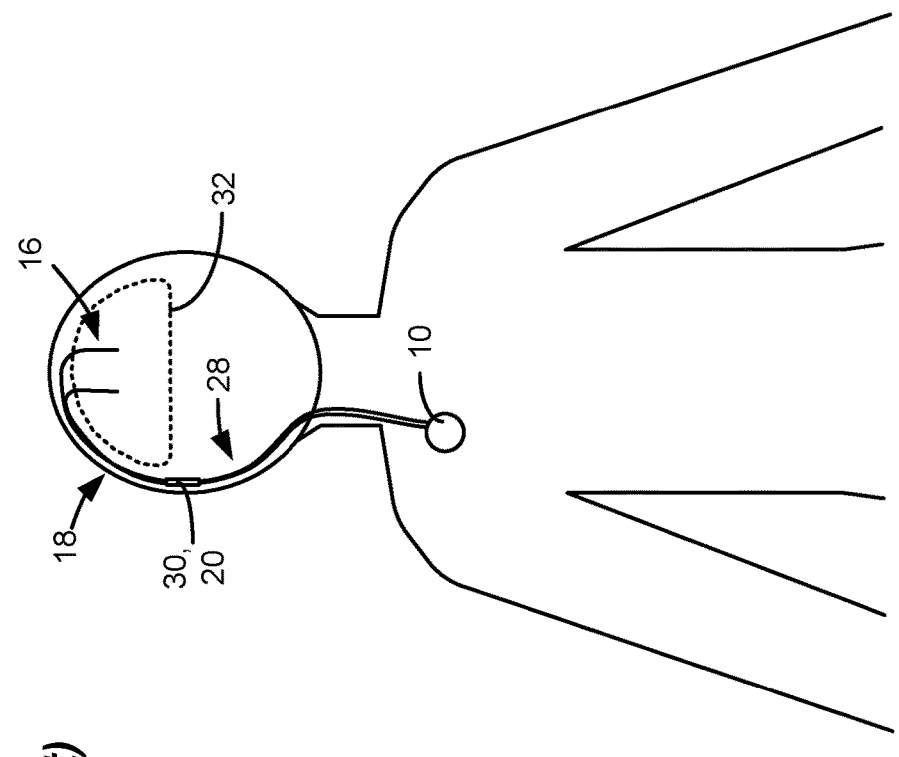
Figure 1 (prior art)
Figure 2 (prior art)

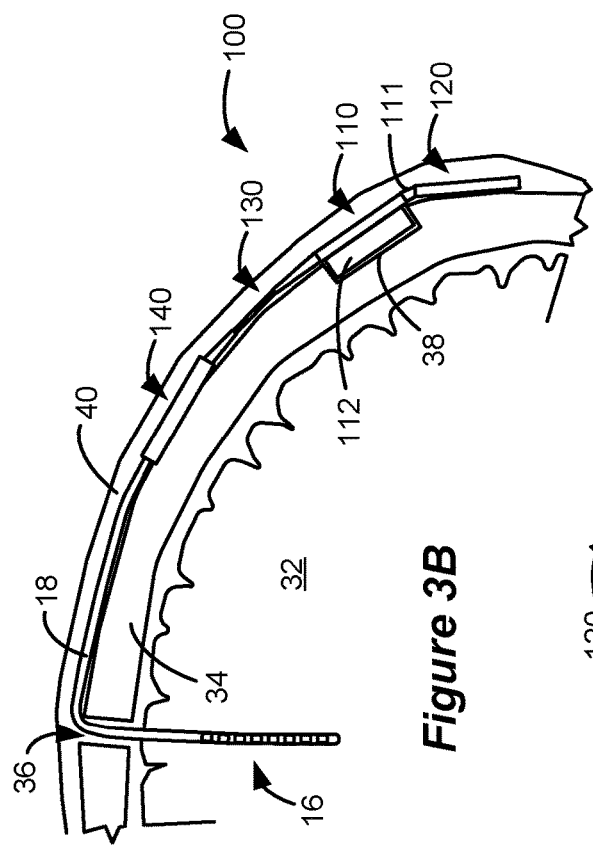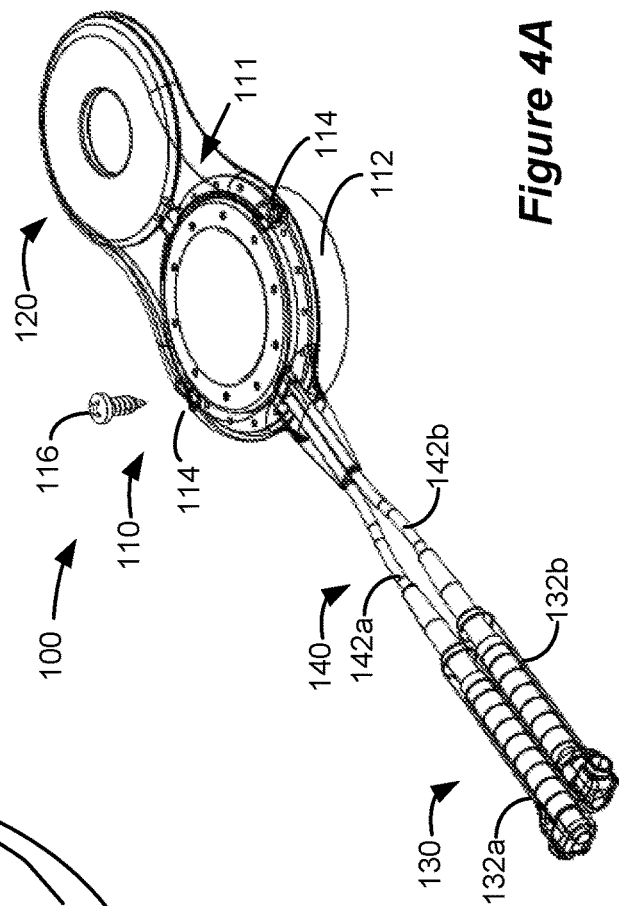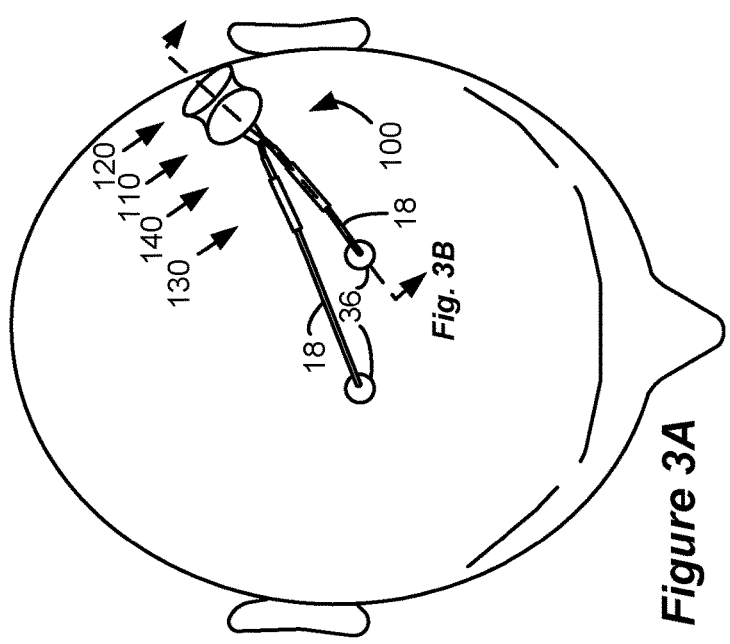

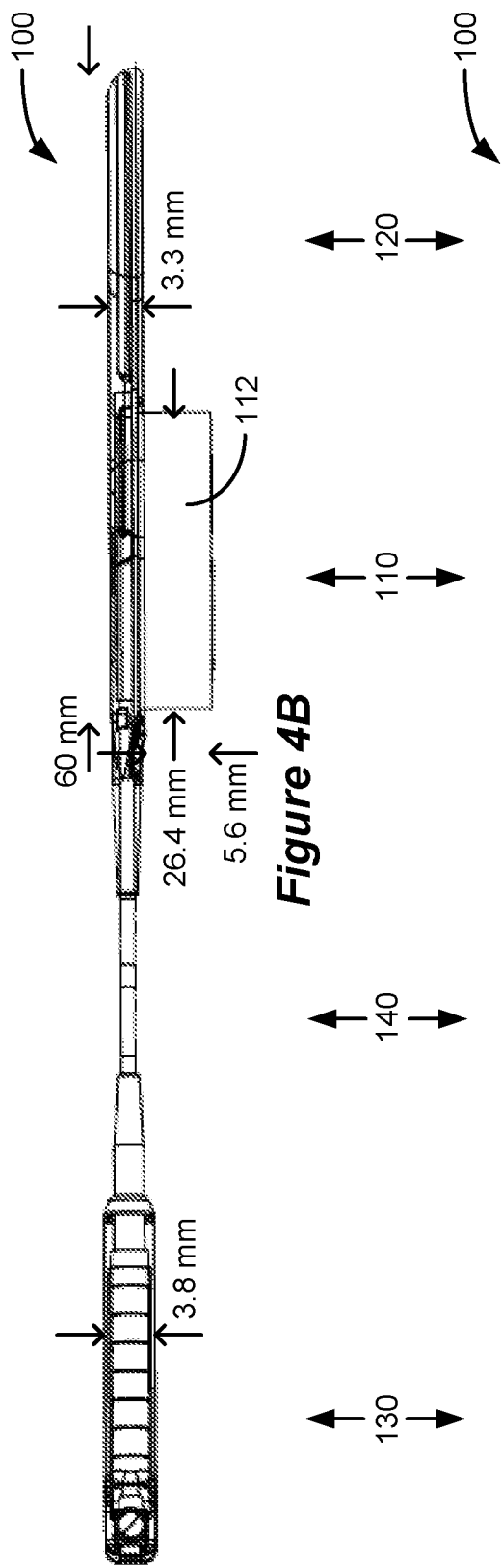
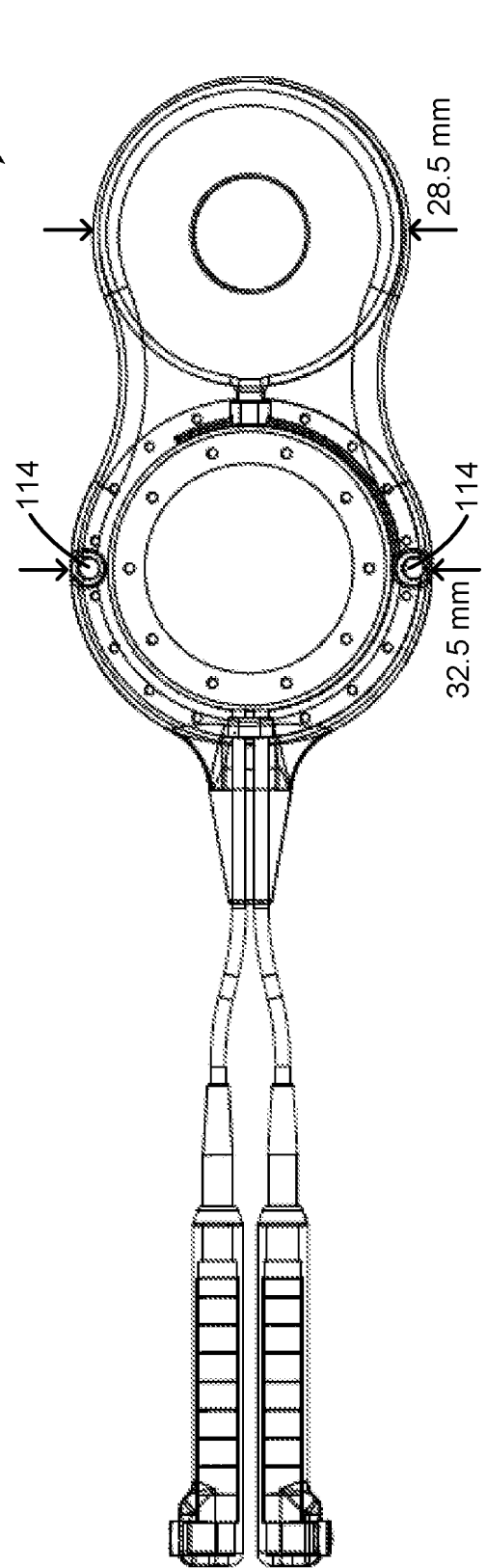
*Figure 4B*
*Figure 4C*

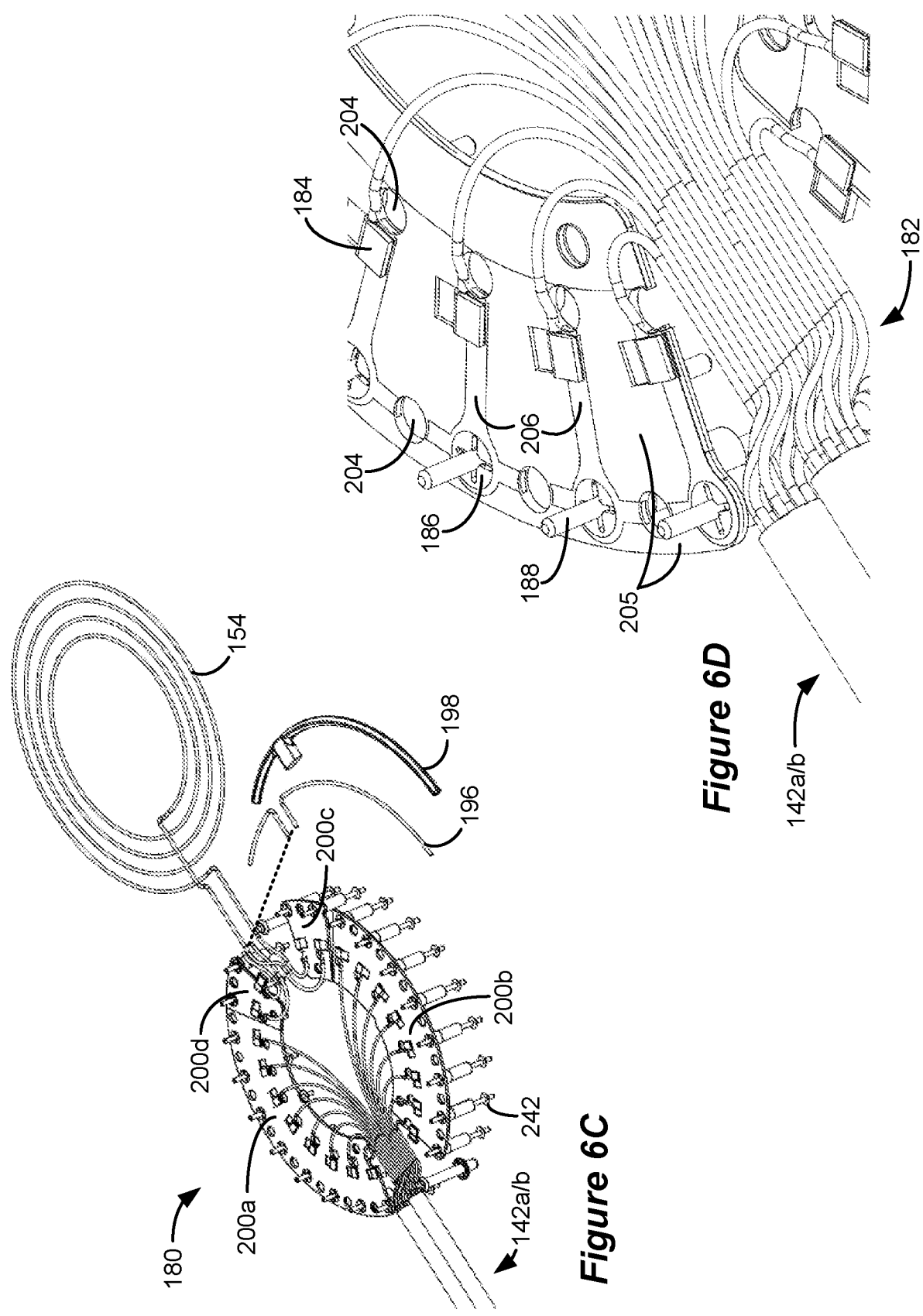

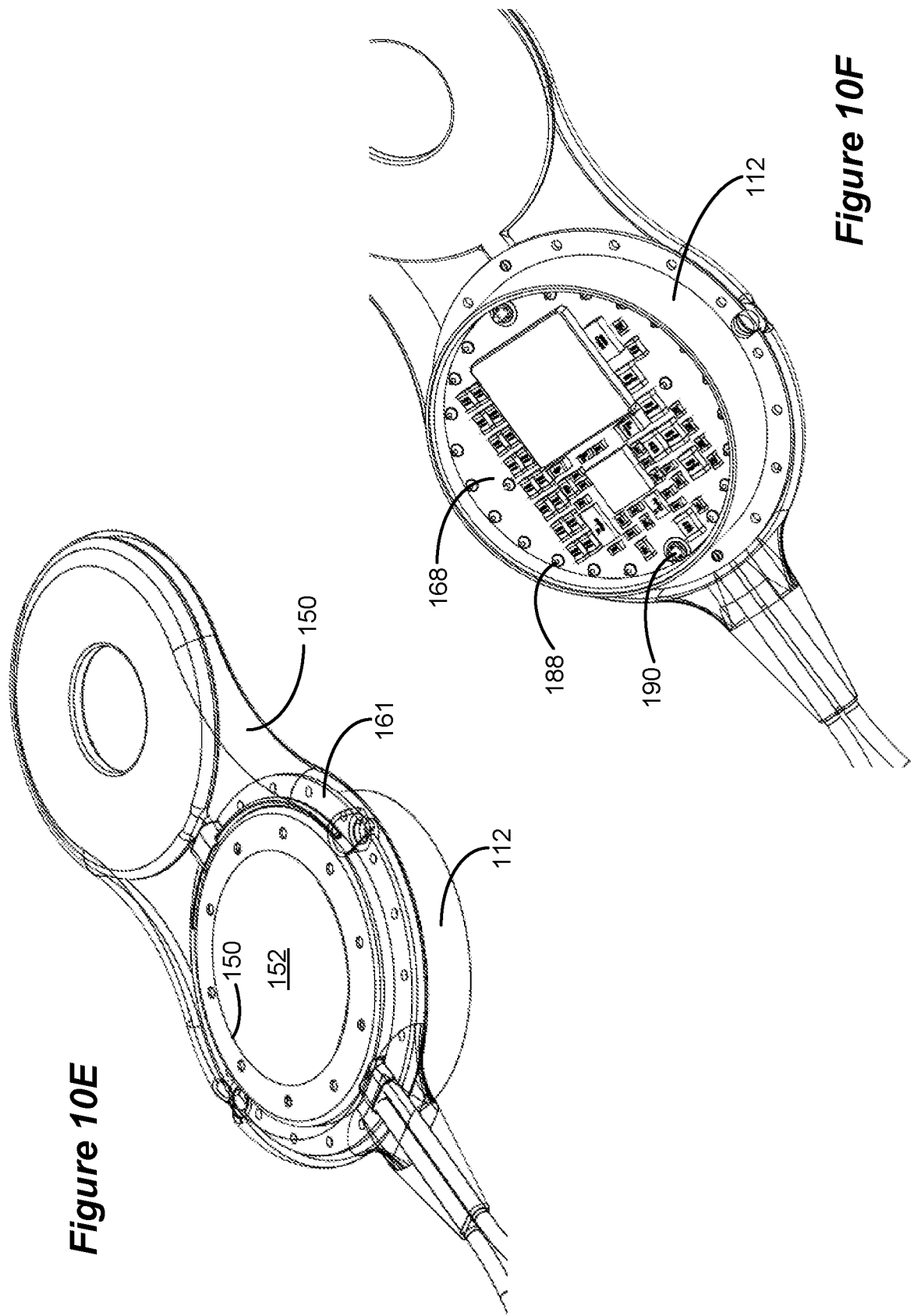

SKULL-MOUNTED DEEP BRAIN STIMULATOR

CROSS REFERENCE TO RELATED APPLICATIONS

This is a non-provisional patent application based on U.S. Provisional Patent Application Ser. No. 62/260,626, filed Nov. 29, 2015, which is incorporated herein by reference in its entirety, and to which priority is claimed.

FIELD OF THE INVENTION

The present application relates to an implantable pulse generator (IPG), such as a Deep Brain Stimulator (DBS).

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and Deep Brain Stimulators (DBS) to treat motor and psychological disorders, and other neural stimulators to treat urinary incontinence, sleep apnea, shoulder subluxation, etc. The description that follows will generally focus on the use of the invention within a Deep Brain Stimulation (DBS) system. However, the present invention may find applicability with any Implantable Pulse Generator (IPG) or in any IPG system.

As shown in FIG. 1, a DBS system includes an Implantable Pulse Generator (IPG) 10, which includes a biocompatible device case 12 comprising titanium for example. The case 12 typically holds circuitry and a battery (not shown), which battery may be either rechargeable or primary in nature. The IPG 10 is coupled to electrodes 16 via one or more electrode leads 18 (two of which are shown). The proximal ends of the leads 18 include electrode terminals 20 that are coupled to the IPG 10 at one or more connector blocks 22 fixed in a header 24, which can comprise an epoxy for example. Contacts in the connector blocks 22 make contact with the electrode terminals 20, and communicate with the circuitry inside the case 12 via feedthrough pins 26 passing through a hermetic feedthrough 28 to allow such circuitry to provide stimulation to or monitor the various electrodes 16.

In a DBS application, as is useful in the treatment of Parkinson's disease for example, the IPG 10 is typically implanted under the patient's clavicle (collarbone), and the leads 18 with electrodes 16 are implanted through holes drilled in the skull in the left and right and side of the patient's brain 32, as shown in FIG. 2. Specifically, the electrodes 16 may be implanted in the subthalamic nucleus (STN), the pedunculopontine nucleus (PPN), the Global Pallidus Interna (GPI), and/or the Ventral Intermediate Nucleus (VIM). In this regard, four leads 18 may be necessary for full coverage, as discussed further in U.S. Patent Application Publication 2013/0184794. Thereafter, a tunnel is formed under the patient's skin and fascia (e.g., over the skull, behind the patient's ear, down the neck) to connect the proximal ends of the leads 18 to the IPG 10. As the distance from the skull holes to the IPG 10 is rather long, extender leads 28 may be employed having receptacles 30 into which the electrode terminals 20 of the leads 18 can be inserted. The extender leads 28 have their own electrode terminals (not shown) to allow connection to the connector blocks 22 in the IPG 10.

While DBS therapy employed in the manner shown can provide effective neurostimulation therapy for a patient, the inventor sees room for improvement. For one, the extended distance between the IPG electronics (under the clavicle) and the site of therapy (the brain, near the top of the head) is inconvenient, as it requires a long tunnel through the patient. Further, if extender leads 28 are used, the possibility of a poor electrical connection between the electrode terminals 20 on the leads 18 and the receptacles 30 of the extender leads 28 can result in the disruption of neurostimulation therapy. Such concerns have caused the inventor to think of new solutions for implementing DBS therapy, and such solutions are disclosed herein.

BRIEF DESCRIPTION OF THE DRAWINGS

FIG. 1 shows an Implantable Pulse Generator such as a Deep Brain Stimulator (DBS), in accordance with the prior art.

FIG. 2 shows the IPG of FIG. 1 as implanted in a patient, in accordance with the prior art.

FIGS. 3A and 3B show an improved IPG as implanted in a DBS patient, in accordance with an example of the invention.

FIGS. 4A-4C show the improved IPG in isolation and in various view, in accordance with an example of the invention.

FIGS. 6A-6D show various electrical connections with the improved IPG, in accordance with an example of the invention.

FIG. 7A shows an underside of the housing of the improved IPG, while

FIGS. 10A-10G show various steps in the construction of the improved IPG, in accordance with an example of the invention.

DETAILED DESCRIPTION OF THE INVENTION

Figure 5:
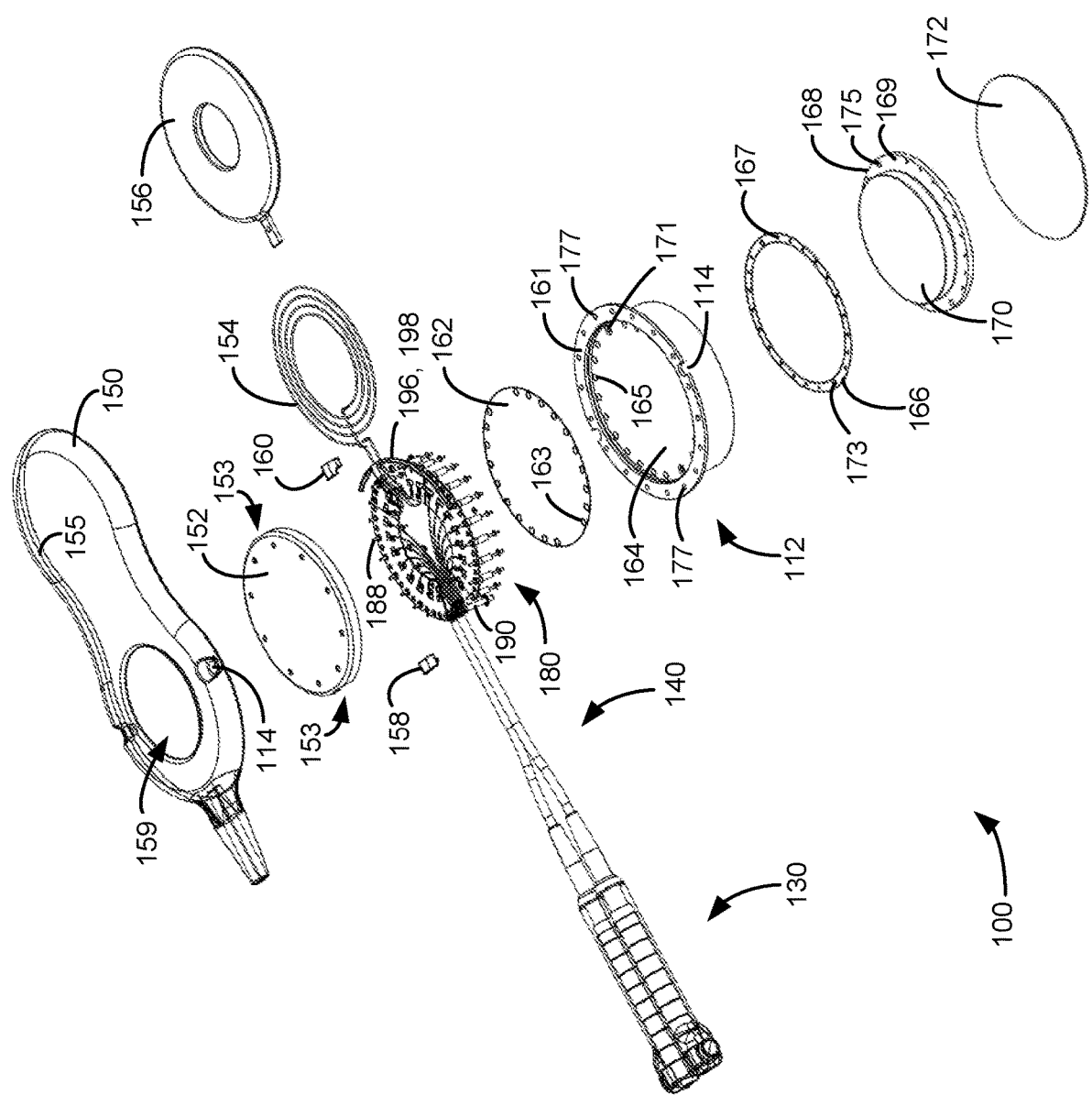
FIG. 5 shows an exploded view of the components of the improved IPG, in accordance with an example of the invention.

A first example of an improved DBS IPG device 100 is shown in FIGS. 3A and 3B as implanted in a patient, and in FIGS. 4A-4C in isolation and in perspective, side, and top-down views respectively. As shown in FIG. 3A, viewing the top of a DBS patient's head, the IPG 100 is designed to lie generally flat against the patient's skull, and preferably above the patient's ear proximate to the temporal or parietal bones. Such placement is preferable because the skull in these locations is generally flat, therefore allowing the IPG 100 to lay relatively flat. However, because the IPG 100 is flexible at certain locations, perfect flatness of the skull is not required, as seen in the cross section of FIG. 3B.

The IPG 100 is generally divided into four sections: an electronics section 110, a charging coil section 120, a connector block section 130, and an electrode wire section 140. Sections 130 and 140 are further comprised in this example of left and right connector blocks 132a and 132b, each coupled to its own electrode wire cable 142a and 142b. In this example, each connector block 132/142 pair can couple to one of the eight-electrode leads 18 illustrated earlier (FIG. 1). However, the number of connector block/electrode wire cable pairs is application specific, and can comprise one or more than two.

As shown in the cross section of FIG. 3B, the IPG 100 is generally flexible at the connection 111 between the electronics section 110 and the charging coil section 120, and also at the electrode wire section 140, which as noted permits implantation of the IPG 10 against the skull even if not perfectly flat. The charging coil section 120 is also generally flexible as it is largely comprised of silicone, as explained in detail later.

Electronics section 110 includes a conductive housing 112, which includes the electronics necessary for proper functioning of the IPG 100. As seen in the various drawings, housing 112 is generally cylindrical, and preferably comprises titanium. The housing 112 is designed to be mounted into a similarly shaped and sized hole 38 formed in the patient's skull 34, as shown in FIG. 3B. The electronics section 110 further includes one or more screw holes 114 (e.g., two as shown) that proceed at least in part through the housing 112, and that receive bone screws 116 (FIG. 4A; only one screw shown) to allow the IPG 100 to be firmly secured to the skull 34 once the subassembly 112 is positioned in the hole 38. In FIG. 3B, the hole 38 in the skull 34 for accepting the housing 112 proceeds only partially through the thickness of the skull 34, but in other examples may proceed all the way through to the dura (not shown) surrounding the brain 32. Notice from FIG. 3B that the IPG 100 is fully implanted between the skull 34 and the skin/fascia 40 on top of the skull.

Before securing of the IPG 100 to the skull 34, the implanting physician will have drilled one or more holes 36 in the skull 34 as shown in FIG. 3A, and will have inserted the distal ends of leads 18 with the electrodes 16 into appropriate locations in the brain 32, as discussed earlier. The leads 18 once properly placed can be secured in holes 36 by the physician using standard means, such as by cementing or plugging. Thereafter, and once the physician has verified the effectiveness of neurostimulation therapy using standard DBS surgical equipment (not shown), the IPG 100 can be secured to the skull 34 as described. Thereafter, proximal ends of the leads 18 with the electrode terminals 20 (FIG. 1) can be inserted into the connector blocks 132a and 132b of the IPG's connector block assembly 130. In this example, both left and right leads 18 are used, and so the IPG 100 includes two connector blocks 132a and 132b in its assembly 130, although as noted earlier this number is variable. Leads 18 may be much shorter than those described in conjunction with the prior art, and extender leads (28, FIG. 2) are not required. Leads 18 may have some slack along the skull 34 as they proceed from the connector block assembly 130 to the holes 36.

IPG 100 is thus implanted much closer to the site of therapy—a few inches rather than a foot or more—and doesn't require a long tunnel through the patient. Further, this shortened distance renders communications 100 between the IPG and the implanted electrodes 16 less complicated and more reliable. Further, the IPG 100 is small in size and volume, as the example dimensions depicted in FIGS. 4B and 4C show. Notice importantly that the electronics section 110 and charging coil section 120 only extended a small distance (e.g., 3.3 mm) above the skull 34's surface when implanted. This low profile is facilitated by the fact that housing 112 of the electronics section 110 is implanted significantly below the skull's surface (e.g., 5.6 mm) in skull hole 38. The connector block assembly 130 also has a relative small profile (e.g., 3.8 mm), and thus the entire IPG 100 is easily accommodated under the patient's skin/fascia 40.

FIG. 5 shows an exploded view of various components of the IPG 100, which are now identified and briefly explained. The function and purpose of these components will also be explained in conjunction with FIGS. 10A-10G, which illustrate sequential steps in the construction of the IPG 100.

Starting from the top of FIG. 5 is a silicone overmold 150 which serves to integrate the electronics 110 and charging coil sections 120, and to provide soft surfaces for portions of the IPG 100 that might come into contact with a patient's tissue/fascia 40. Screw holes 114 referred to earlier are seen in the overmold 150, as well as partially formed in a lip 161 of the housing 112. Alternatively, if lip 161 is larger or the bone screws 116 (FIG. 4A) smaller, screw holes can be fully formed in the lip. Top cover 152, preferably comprising titanium, is eventually laser welded to the top of the housing 112, and includes two slots 153 to allow for the passage of cabling to the electrode wire section 140 and to antennas 154 and 196, as explained further below. Top cover 152 and a feedthrough 164 portion of the housing 112 create a cavity 201 (FIGS. 7B & 7C) in which electrical connections 180 (described below) can be housed. The overmold 150 may further include a hole 159 to allow the grounded housing at top cover 152 to be tied to the patient's tissue 5.

Charging coil section 120 includes a charging coil antenna 154 within a silicone overmold 156, which is encompassed within overmold 150 during assembly. The charging coil antenna 154 is used to receive a magnetic field from a power source external to the patient (not shown), and is preferably used to charge the IPG 100's battery 170. Alternatively, the IPG 100 may include a primary (non-rechargeable) battery 170, in which case charging coil antenna 154 would be unnecessary. Battery 170 is preferably coin shaped as shown to better integrate with a circular printed circuit board 168 within the housing 112. However, IPG 100 may also lack a battery 170, and instead be designed to continually receive a magnetic field at charging coil antenna 154 from the external power source to provide the IPG the power it needs to function. In one example, battery 170 is rechargeable, with a capacity of 59 mAh.

Bi-directional data communications with the IPG 100 is facilitated by the use of a short-range RF antenna 196 that may include its own silicone overmold 198. Data antenna 196 is preferably configured as a dipole antenna. The data antenna 196 is preferably positioned outside of the top cover 152 and housing 112, and is preferably curved to follow at least a portion of the circular contour of the periphery of the top cover 152. Positioning the data antenna 196 outside of conductive components such as the top cover 152 and the housing 112 keeps such components from attenuating communications to and from the antenna 196. In one example, data antenna 196 can operate pursuant to a Bluetooth communications protocol, although other short-range RF protocols could be used as well, such as Zigbee, MICS, WiFi, etc. Alternatively, data communications can be enabled via magnetic fields received and transmitted from the charging coil antenna 154, in which case data antenna 196 may be unnecessary. Further details concerning external devices with which the IPG 100 can communicate, such as external chargers for providing power (via a magnetic field), patient external controllers, and clinician programmers, are disclosed in U.S. Patent Application Publication 2015/0360038, which is hereby incorporated by reference in its entirety.

Various electrical connections 180 are established inside the electronics section 110, including connections to the electrode wire section 140 and to the antennas 154 and 196. Such signals ultimately attach to various feedthrough pins 188, as described in further detail with reference to FIGS. 6A-6D. A cable retainer clip 158 and an antennas retainer clip 160, both preferably formed of polyether ether ketone (PEEK) and held within the overmold 150, secure connections to the electrode wire cables 142a and 142b and to the wires associated with antennas 154 and 196. As best shown in FIG. 7C, a wedge at the bottom of the clips 158 and 160 press fits into holes 177 formed on the lip 161 of the housing 112.

Figure 7B:
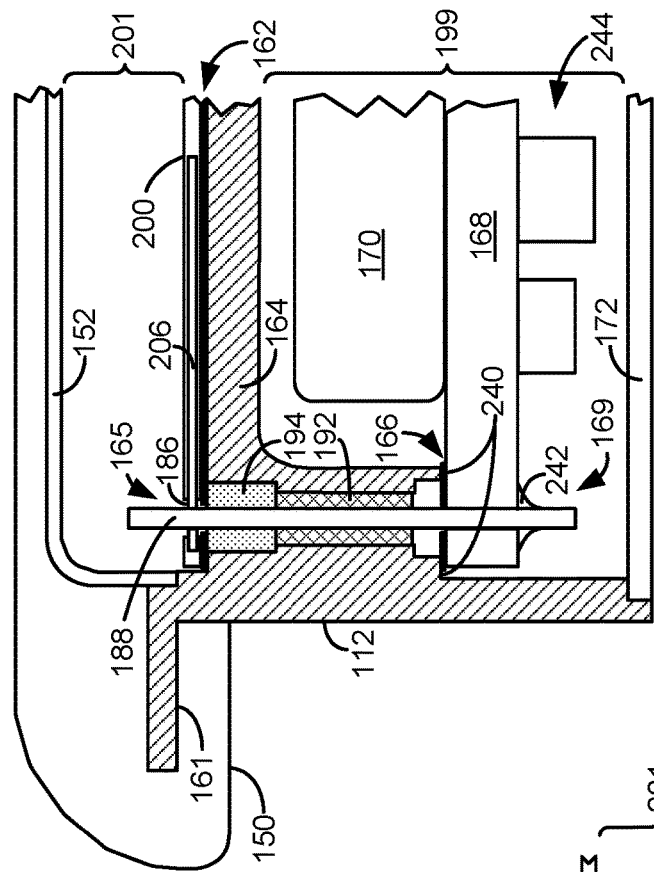
FIGS. 7B and 7C show cross sections through a feedthrough pin and a ground pin respectively, in accordance with an example of the invention.

An insulator disk 162, also preferably formed of PEEK, intervenes between the electrical connections 180 and a feedthrough 164 formed in a top surface of the housing 112. The insulator disk 162 and the feedthrough 164 contain holes 163 and 165 respectively to accommodate the passage of the feedthrough pins 188 therethrough, which pins 188 may comprise titanium or copper for example. Holes 171 in the feedthrough 164 (e.g., two, although more or less could be used) are configured to receive ground pins 190, as discussed subsequently. The lip 161 of the housing 112 is encompassed within the silicone overmold 150 during assembly, as best seen in FIGS. 7B and 7C. In the example shown the feedthrough 164 is integral with the housing 112 and the two are formed as one piece. However, this is not strictly necessary, and feedthrough 164 could for example be welded into place within the housing 112.

A printed circuit board (PCB) 168 is located below the feedthrough 164 inside of the housing 112, and may carry battery 170 (if present) to power the IPG 100. The top of the PCB 168 can include an insulator ring 166, preferably formed of Kapton™, with holes 167 and 173 allowing the feedthrough pins 188 and the ground pins 190 respectively to pass therethrough. The feedthrough pins 188 and the ground pins 190 connect to the PCB 168 at holes 169 and 175 respectively. A bottom cover 172 is laser-weldable to the bottom of the housing 112. This creates a cylindrical and hermetically sealed cavity 199 (FIGS. 7B & 7C) bounded by the parallel planes of the feedthrough 164 and the bottom cover 172 and the circular sidewalls of the housing 112 in which the PCB 168 and battery 170 can be safely located. Note that housing 112 complete with its top cover 152 and bottom cover 172 may also be referred to as the "housing."

Figure 6A:
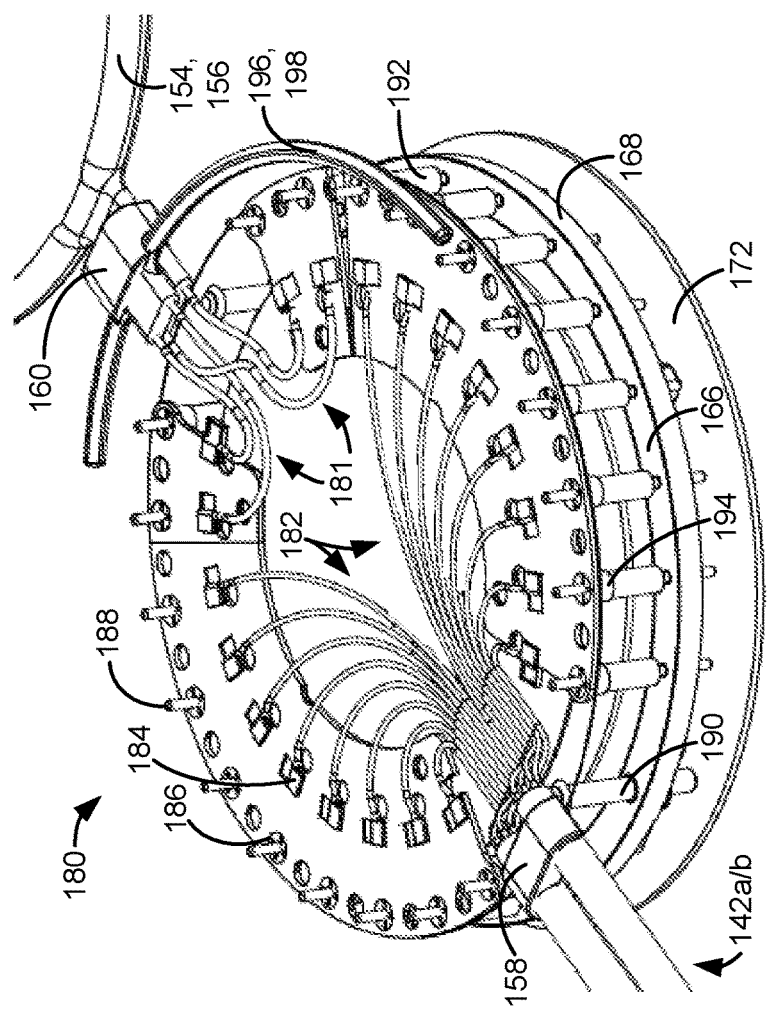

FIGS. 6A-6D show further details of the electrical connections 180 with the housing 112 removed for easier viewing. Electrode wires 182 from the electrode wire cables 142a and 142b (e.g., 8 wires in each) and antenna wires 181 from the data antenna 198 and the charging coil antenna 154 (e.g., four wires, comprising the ends of the antennas) are connected to conductive terminals 184 formed in one or more substrates 200. As shown in FIG. 6C, four substrates 200a-d are used in this example, with substrate 200a connecting to the electrodes wires in electrode wire cable 142a; 200b connecting to the electrode wires in electrode wire cable 142b; 200c connecting to the ends of the charging coil antenna 154; and 200d connecting to the data antenna 196.

As best seen in FIG. 6D, the conductive terminals 184 may comprise crimps (tie bars) formed in conductive traces 206 in the substrates 200, which are crimped (bent) over the ends of the wires 181 and 182. Traces 206 in turn lead to contacts 186 that connect to the feedthrough pins 188 that are eventually connected to the IPG's PCB 168. In the example shown, contacts 186 have a cross shape through which the ends of the feedthrough pins 188 can be pressed to provide electrical and mechanical connections, although these connections may also later be soldered or laser welded. Still referring to FIG. 6D, the substrates 200a-d can in one example comprise a metal lead frame that is dipped in silicone 205 to cover and insulate the traces 206. Once the silicone 205 has cured, the silicone over the crimps 184 may be excised, and holes 204 may then be formed (e.g., by laser ablation) to disconnect the various traces 204 in the lead frame from each other.

Such means of establishing electrical connections 180 is not strictly necessary, and other variations can be made. For example, the substrates 200 may instead comprise more typical PCBs, and may be consolidated into a single substrate, although forming them in pieces (200a-d) facilitates IPG construction as shown later. Connection of the wires 181, 182 and feedthroughs 188 to the substrates 200 can also be made in other ways, for example, by soldering.

Figure 6B:
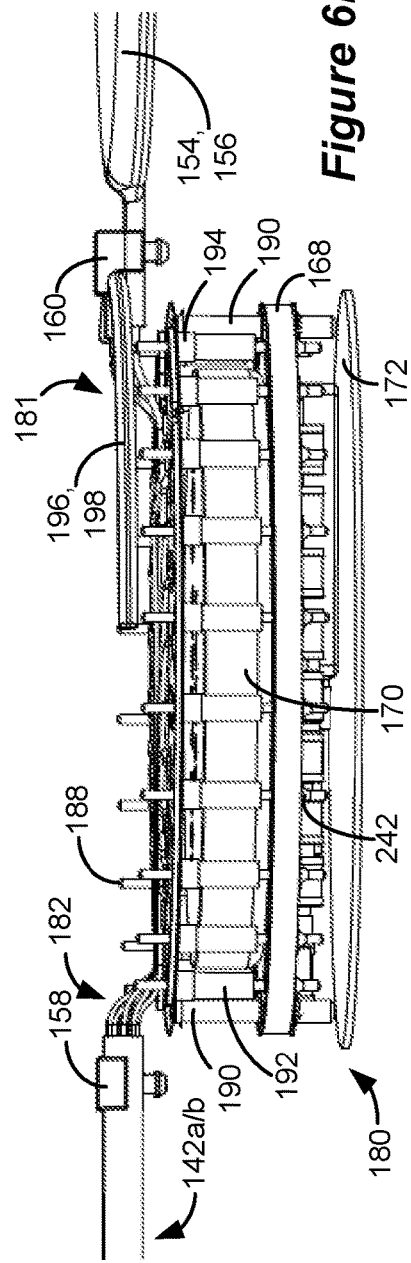

Referring to FIGS. 6A and 6B, each feedthrough pin 188 ultimately connects to its corresponding node (at holes 169) on the PCB 168. Each feedthrough pin 188 is further surrounded by a ceramic bead 194 and a tube 192 preferably formed of Kryoflex™ ceramic. The ceramic beads 194 and tubes 192 are located within holes 165 in the feedthrough 164 (FIG. 5), although again the housing 112 and its feedthrough 164 is not shown in FIG. 6A or 6B for clarity. Once the ceramic beads 194 and tubes 192 are positioned with the holes 165, and the feedthrough pins 188 are positioned therethrough, they are sintered (melted) to form a hermetic seal around the feedthrough pins 188. As well as providing a good hermetic seal for the feedthrough pins 188, the ceramic beads 194 and tubes 192 are serve to insulate the feedthrough pins 188 from the conductive body of the housing 112, which is preferably grounded by the ground pins 190, as explained further below.

Figure 7A:
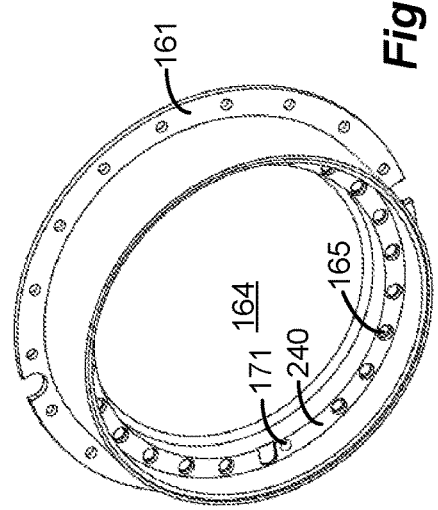
Figure 7C:
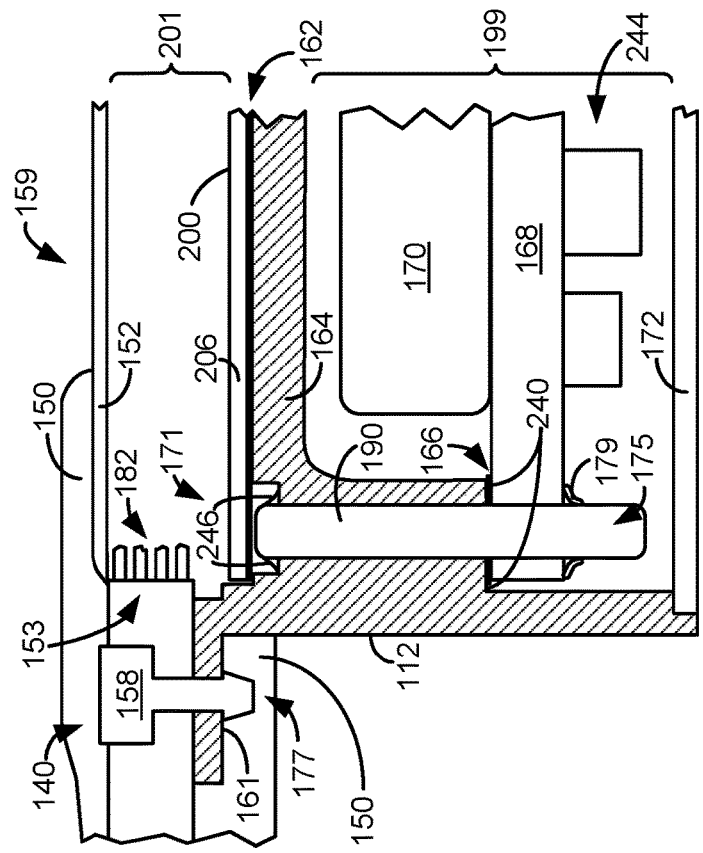

Further details of how the feedthrough pins 188 and ground pins 190 pass through feedthrough 164 and connect to the PCB 168 are shown in FIGS. 7A-7C. First, note in FIG. 7A that the underside of the housing 112 includes a ledge 240. The top surface of the PCB 168 will rest against this ledge 240, with insulator disk 166 intervening to prevent to two from shorting, as shown in FIGS. 7B and 7C. FIGS. 7B and 7C respectively show cross sections through a feedthrough pin 188 and a ground pin 190. Notice in FIG. 7B how the sintered ceramic bead 194 and tube 192 insulates the feedthrough pin 188 from shorting to the conductive material of the housing 112. By contrast, no such insulation occurs around ground pin 190 as shown in FIG. 7C, as it is desirable that the ground pin 190 pass ground from the PCB 168 electronics 244 to the conductive material of the housing 112. Notice further that the feedthrough pins 188 in FIG. 7B are affixed to the PCB 168 in holes 169 and to appropriate corresponding PCB signals using conductive epoxy joints 242. Ground pins 190 meet with a ground signal on the PCB at conductive retaining springs 179 at the holes 175 in PCB 168. Ground pins are further connected to the housing 112 at conductive joints 246, as shown in FIG. 7C. In an alternative embodiment, ground pins 190 may short to the body of the housing 112 without penetrating fully through the body, and thus holes 171 may not proceed through to the top cavity 201. This alternative may be preferred so that hermeticity of cavity 199 at the location of the ground pins 190 is not compromised.

Figure 8:
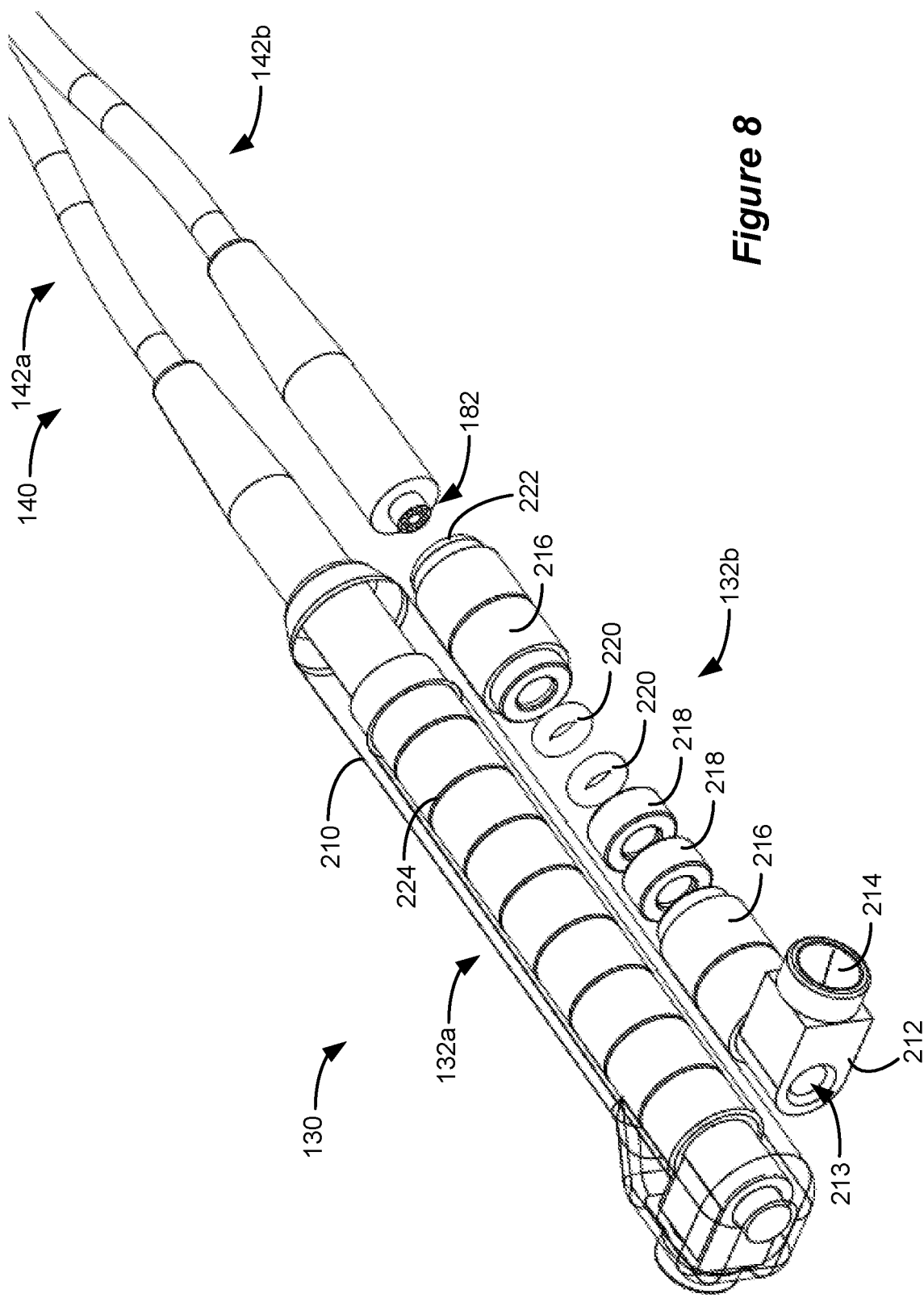
FIG. 8 shows components within a connection block section of the improved IPG, in accordance with an example of the invention.

FIG. 8 shows further details of the connector block section 130, with some of the components of connector block 132b removed for easier viewing. Covering the components of the connector blocks 132a and 132b is an overmold 210, which may be made of silicone for example. The proximal end of a lead 18 with its electrode terminals 20 (FIG. 1) is inserted in an opening 213 of a lock 212 which can receive a set screw (not shown) at perpendicular port 214 to hold the lead 18 in place after it is fully inserted to an end stop 222 in one of the connector blocks. Each of the electrode terminals 20 when fully inserted will meet with a corresponding spring contact 220 formed of a deformable conductive material. Each spring contact 220 is encased in a conductive housing 218, and insulating seals 216 intervene between adjacent conductive housings 218 to prevent them from shorting. Although not shown, electrode wires 182 from the electrode wire cables 142a and 142b proceed between the overmold 210 and the insulating seals 216, and each wire connects to a corresponding conductive housing 218/spring contact 220 at gaps 224 between the seals 216.

Figure 9:
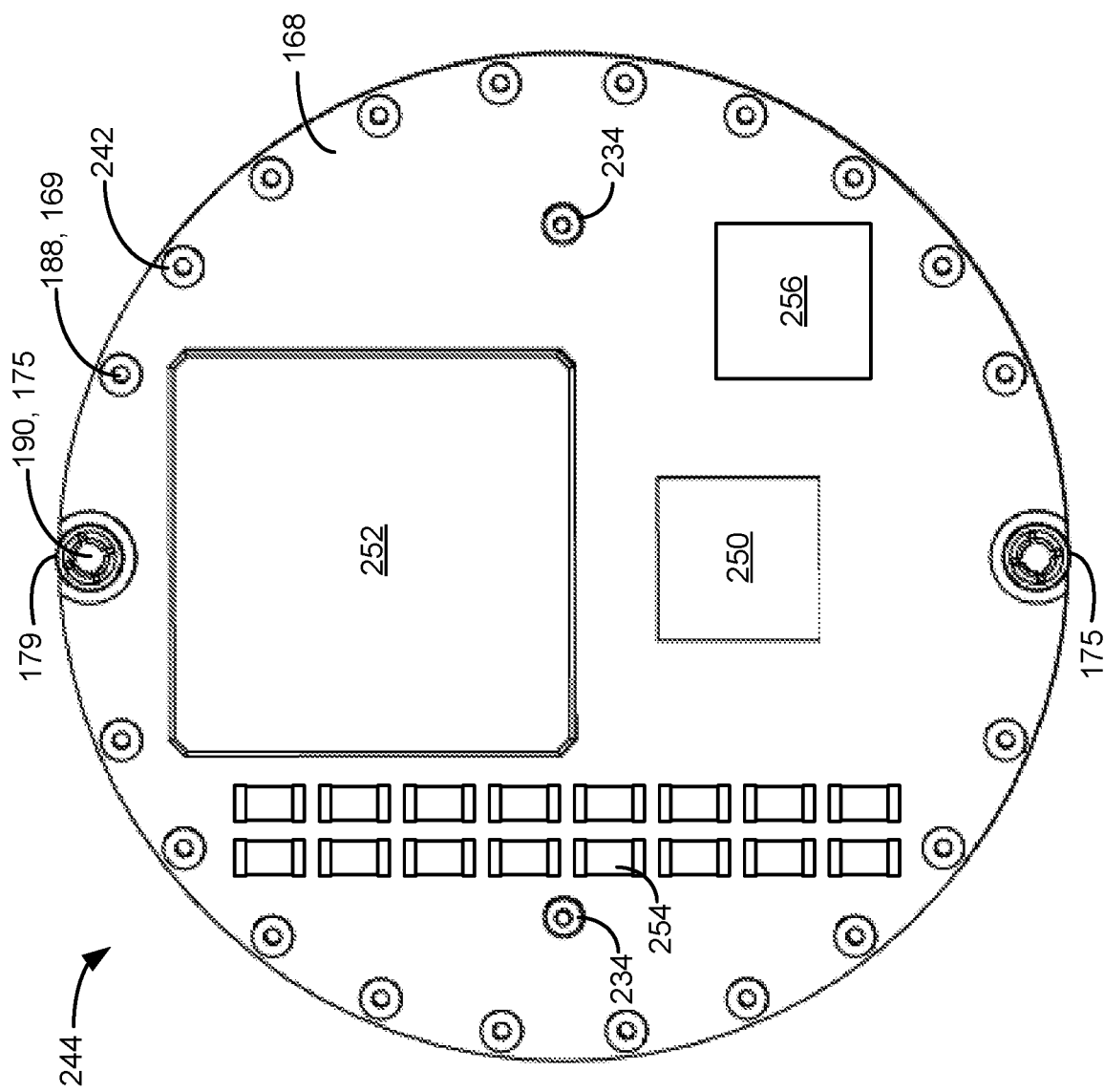
FIG. 9 shows details of a Printed Circuit Board (PCB) within the IPG, in accordance with an example of the invention.

FIG. 9 shows the underside of the PCB 168, and the electronics 244 it carries. The battery 170 is on the top side of the PCB 168 and thus not in view in FIG. 9, but its solder holes 234 can be seen. Note that the battery 170 and electronics 244 can be reversed on the PCB 168 with the former on the underside and the latter on the top side, or the battery 170 and electronics 244 could be distributed on the PCB 168 in other fashions. Further, note that the IPG 100 need not include a battery in a continuous power example as discussed earlier.

The IPG 100 can operate as described in various manners in U.S. Patent Application Publication 2013/0184794, which is incorporated herein by reference in its entirety, and FIG. 9 shows many of the components discussed in that publication, including: a microcontroller 250; an Application Specific Integrated Circuit (ASIC) 252, which among other details provides output currents to the electrodes 16; DC-blocking capacitors 254 through which output currents are routed on the way to electrodes 16; etc. Also shown is a Bluetooth integrated circuit 256, which connects to the data antenna 196 (FIG. 5) and provides modulation and demodulation circuitry to assist in wireless data transmission and reception. Other electronics 244 such as voltage regulators, temperature measuring circuitry, timing crystals, etc., are not shown for simplicity. Notice that the feedthrough pins 188 and their receiving holes 169 are shown along with the conductive epoxy 242 used to mechanically and electrically couple the feedthrough pins to the PCB 168. Likewise, ground pins 190 and their receiving holes 175 are shown along with the retaining springs 179 used to mechanically and electrically couple the ground pins to the PCB 168.

Figures 10A, 10B:
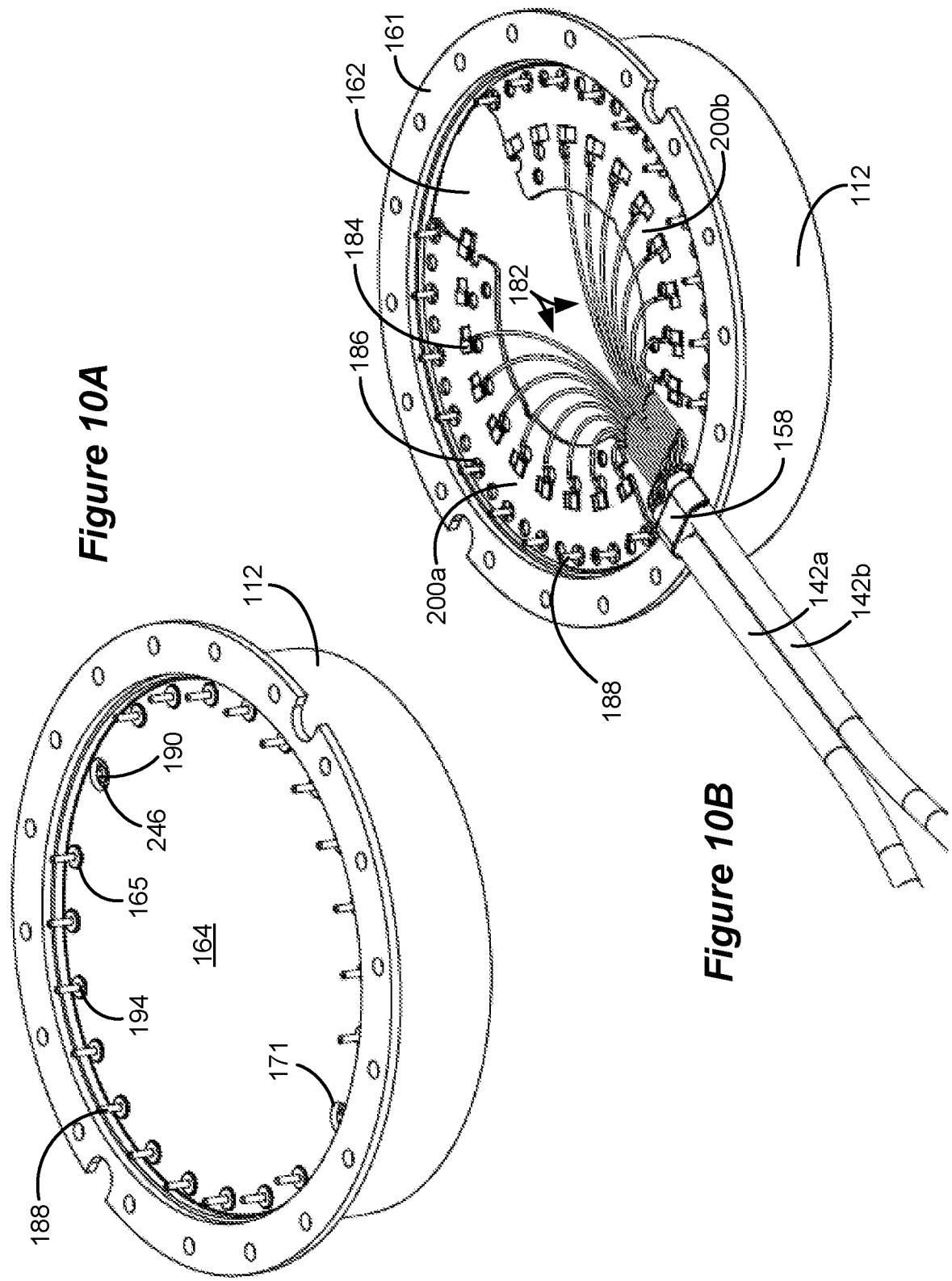

With components of the IPG 100 explained, attention can be turned to the manner in which the IPG 100 is assembled with reference to FIGS. 10A-10G. Assembly starts as shown in FIG. 10A by affixing the feedthrough pins 188 and ground pins 190 through the feedthrough 164 of the housing 112. Ceramic beads 194 and tubes 192 are placed in holes 165 in the feedthrough, and the feedthrough pins 188 are placed through their centers. Ground pins are placed through holes 171, and conductive joints 246 are applied. Thereafter, the subassembly is heated to sinter the ceramic beads 194 and tubes 192 and the conductive joints 246, thus sealing all feedthrough 164 holes 165 and 171 with good hermeticity.

Next, and referring to FIG. 10B, the insulator disk 162 is placed over the feedthrough 164, with feedthrough pins 188 sticking through the disk's holes 163 (FIG. 5). Thereafter, substrates 200a and 200b are positioned in place by pressing the feedthrough pins 188 through its cross-shaped contacts 186. The electrode wire cables 142a and 142b are affixed to the lip 161 of the housing 112 using cable retainer clip 158, i.e., by press fitting the clip through one of the lip's holes 177 (see FIG. 7C). It is preferable that the connector blocks 132a and 132b of the connector block assembly 130, the electrode wire cables 142a and 142b of the electrode wire assembly 140 and the substrates 200a and 200b be preassembled prior to coupling to the housing 112. For example, connector block 132a (not shown in FIG. 10B) is connected to one end of the electrode wires 182 in electrode wire cable 142a, while the other ends are connected to substrates 220a via conductive terminals (crimps) 184 as explained earlier. However, pre-preparation of such subassemblies is not strictly required.

Figures 10C, 10D:
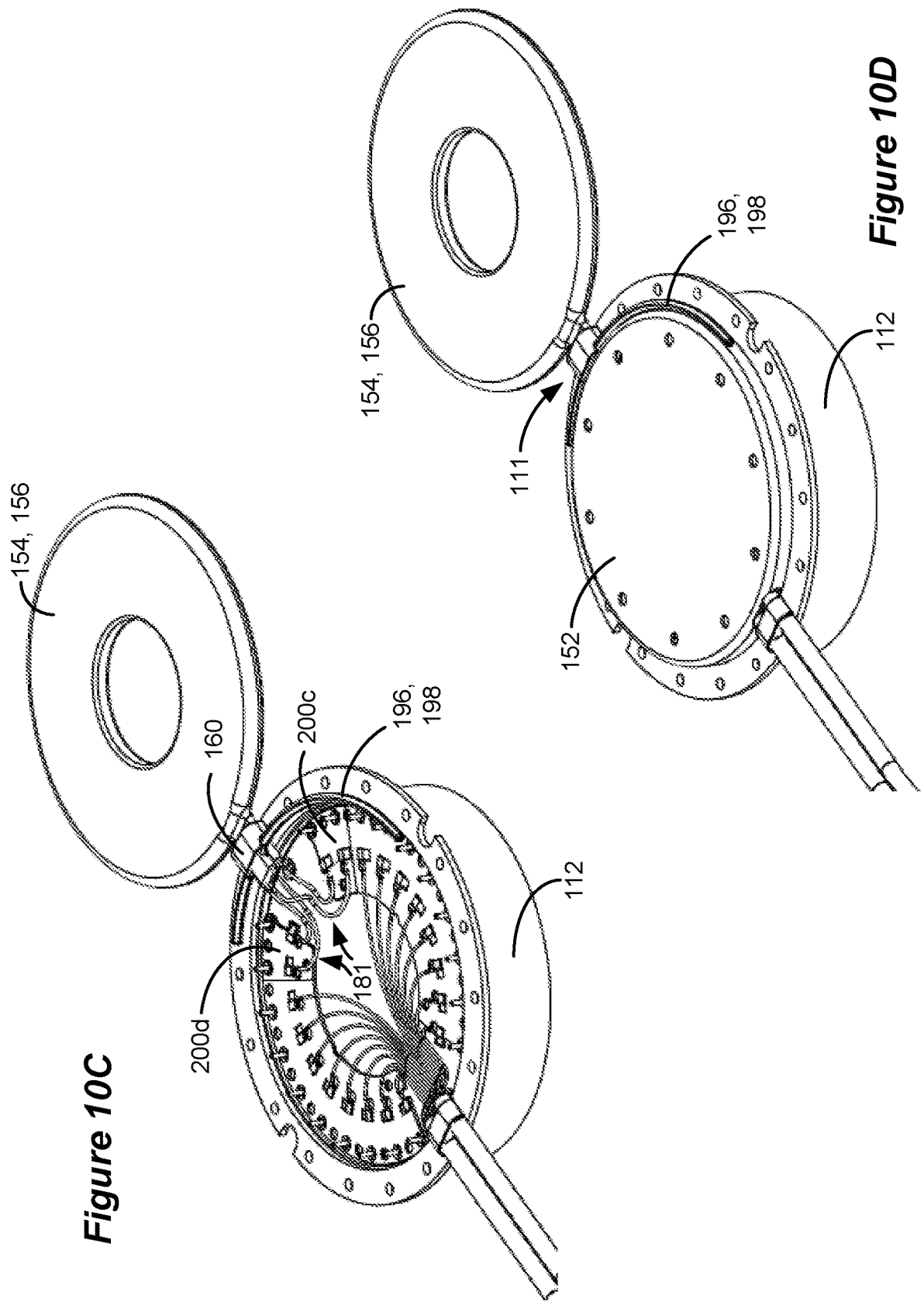

Referring next to FIG. 10C, substrates 200c and 200d are positioned in place similarly to the substrates 200a and 200b of FIG. 10B, thus coupling antenna wires 181 to the assembly. Substrate 200c can be placed and connected first, and is preferably preassembled including charging coil antenna 154 and its overmold 156. Then substrate 200d can be placed, again preferably preassembled with data antenna 196 and its overmold 198. Overmold 198 may overlie overmold 156 at the location of antenna retainer clip 160, which is fastened to the lip 161 of the housing 112. If necessary the connections between the feedthrough pins 188 and the contacts 186 can be soldered or laser welded at this point.

Next, and referring to FIG. 10D, the top cover 152 is positioned in place, and laser welded to the housing 112. Notice that the data antenna 196 and its overmold 198 remain outside of the top cover 152, with laser welding occurring below them. Note also that connection 111 between the main electronic housing and the charging coil antenna 154 remains flexible as it only includes the silicone overmold 156 and the flexible ends of the wires of the charging coil 154. As described earlier, flexibility at connection 111 assists in allowing the IPG 100 to conform to the contour of the patient's skull.

Next, overmold 150 can be formed over and encompass at least a part of the housing and charging coil sections, as shown in FIG. 10E, with lip 161 of the housing 112 and edges of charging coil overmold 156 being encompassed by the overmold 150 (see FIGS. 7B & 7C). Note that overmold 150 need not encompass the entirety of the top cover 152, although it could. At this point, leak testing can be performed to ensure that cavity 201 formed between the top cover 152 and the feedthrough 164 of the housing 112 is suitably hermetic. Electrical testing may also be performed by connecting a tester to the feedthrough pins 188 and ground pins 190 exposed on the underside of the assembly to ensure that no unwanted short or open circuits have occurred in the electrical connections 180.

Figure 10G:
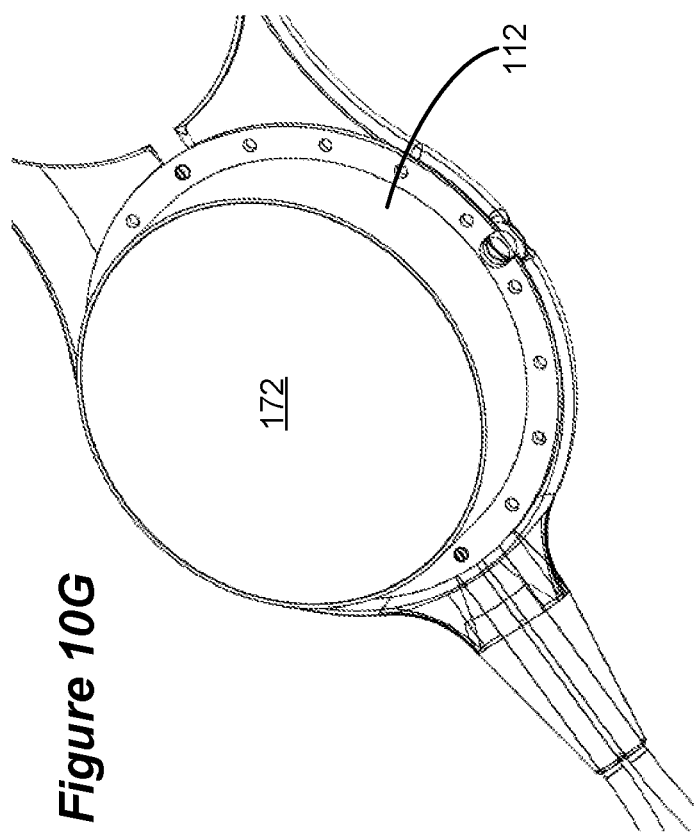

Next, the insulator disk 166 is positioned on ledge 240 on the underside of the housing 112 as explained earlier (see FIGS. 7B & 7C), and then the fabricated PCB 168 is placed over disk 166, as shown in FIG. 10F. Placement of the PCB 168 includes ensuring that the feedthrough pins 188 and ground pins 190 pass through holes 169 and 175 on the PCB 168. At that point, conductive epoxy joints 242 can be added to the feedthrough pins 188, and possibly also to the conductive retaining springs 179 through which the ground pins 190 pass. Such contact points can alternatively be soldered. Thereafter, bottom cover 172 is laser welded to the underside of the housing 112, as shown in FIG. 10G, thus forming hermetic cavity 199 (see FIGS. 7B & 7C). Hermetic and electrical testing may then occur again, with electrical testing occurring by way of wireless communication with the data antenna 196.

Notice that the cylindrical cavities 199 and 201 are formed using a top cover 152, feedthrough 164, and bottom cover 172 that lie in planes that are parallel. Cavity 199 (between the feedthrough 164 and the bottom cover 172) and cavity 201 (between the feedthrough 164 and the top cover 152) are both hermetic, but note that the hermeticity of cavity 199 is preferably superior. This is because cavity 199 is bounded by welds and by the sintered ceramic beads 194 and tubes 192, thus providing excellent hermeticity for the PCB 168, its electronics 244, and the battery 170. The hermeticity of cavity 201 by contrast is not as strong. This is because slots 153 (FIG. 5) in the top cover 152 provide a potential path for ingress, even if blocked by the electrode cable wires 142a and 142b, the overmolds 156 and 198, and/or overmold 150. Nonetheless, hermeticity in cavity 201 is not as crucial in cavity 199 contains the electronics 244.

To this point, IPG 100 has been illustrated as having a separate electronics section 110 and charging coil section 120 that are non-overlapping. That is, the sections 110 and 120 are next to each other, and charging coil section 120 lie in a small plane as the housing 112. This is beneficial because it frees the charging coil 154 of conductive structures that might interfere with the receipt of magnetic fields, or cause unnecessary heating.

Figure 11:
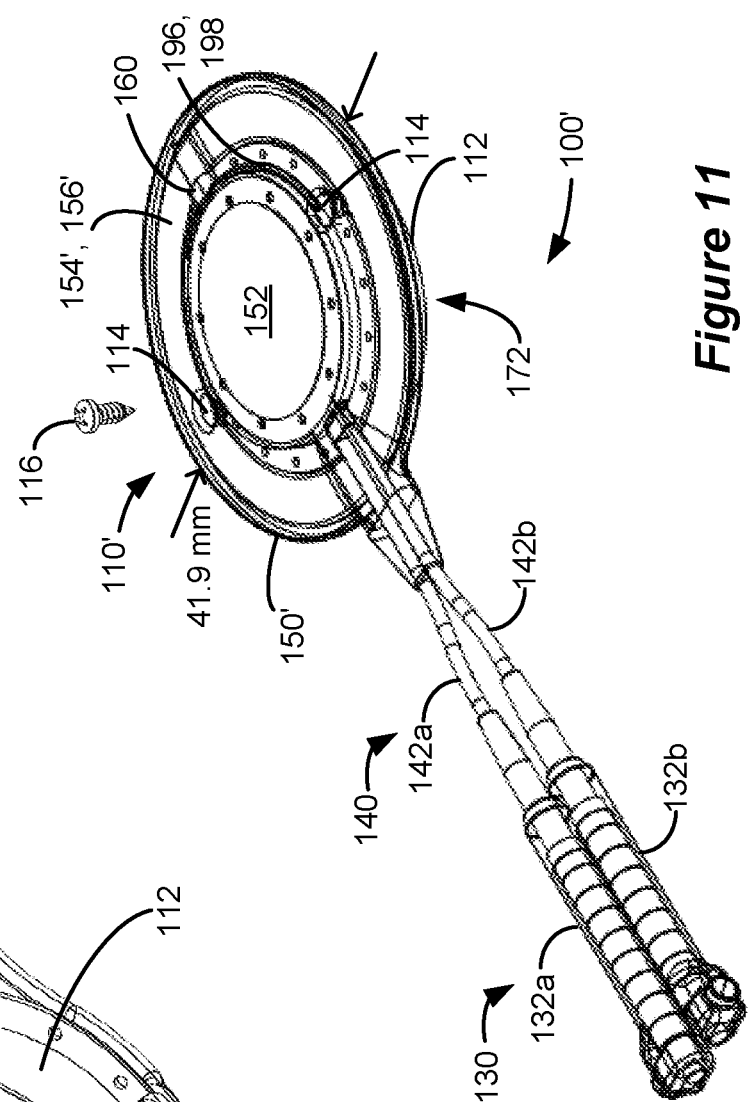
FIG. 11 shows an alternative design for the improved IPG in which the charging coil encircles the housing, in accordance with an example of the invention.

Nonetheless, such a configuration is not strictly necessary, and FIG. 11 shows an alternative construction for an IPG 100' in which electronics section 110 is effectively located in the center of the charging coil section 120. Specifically, IPG 100' includes a combined electronics and charging coil section 110' in which the charging coil 154' and its overmold 156' encircle the housing 112. Construction is otherwise similar to that illustrated earlier for IPG 100, and many of the components can remain unchanged, such as the connector block section 130, and the electrode wire section 140. However, the shape of overmold 150' is now generally circular to match the circular shape of the outer charging coil 154'/overmold 156'. Nonetheless and as before, the housing 112 may still be implanted within a hole 38 in the skull 34 (see FIG. 3B), and fastened there by bone screws 116 passing through screw holes 114. Moreover, the IPG 100' is useable on portions of the skull that are not flat, because electrode wire cables 142a and 142b are still flexible. Further, the charging coil overmold 156' and overmold 150', being silicone, can also deform to some degree.

While the invention herein disclosed has been described by means of specific embodiments and applications thereof, numerous modifications and variations could be made thereto by those skilled in the art without departing from the scope of the invention set forth in the claims.

What is claimed is:

1. An implantable pulse generator, comprising:
 a conductive housing comprising a conductive top cover, a conductive bottom cover, and a feedthrough, wherein a first cavity is enclosed between the top cover and the feedthrough, and wherein a second cavity is enclosed between the bottom cover and the feedthrough, wherein the feedthrough, the top cover and the bottom cover lie in planes that are parallel;
 a plurality of feedthrough pins passing through the feedthrough between the first cavity and the second cavity;
 a circuit board comprising pulse generator circuitry in the second cavity connected to each of the plurality of feedthrough pins;
 a battery in the second cavity configured to provide power to the pulse generator circuitry;
 at least one electrode wire cable extending outwardly from the housing, wherein each electrode wire cable comprises a plurality of electrode wires coupled by electrical connections in the first cavity to some of the feedthrough pins; and
 wherein each at least one electrode wire cable comprises a connector block, wherein each connector block comprises an opening configured to receive a proximal end of a lead, the lead comprising a distal end including electrodes for stimulating a patient's tissue, wherein each of the plurality of electrode wires in an electrode wire cable connected to a connector block are coupled to contacts in that connector block.

2. The implantable pulse generator of claim 1, wherein the first and second cavities are cylindrical.

3. The implantable pulse generator of claim 1, further comprising an insulator between the electrical connections and the feedthrough.

4. The implantable pulse generator of claim 1, wherein the circuit board rests on a ledge of the housing inside the second cavity.

5. The implantable pulse generator of claim 4, further comprising an insulator between the circuit board and the ledge.

6. The implantable pulse generator of claim 1, further comprising a charging coil antenna outside of the housing, wherein the charging coil antenna is located in a same plane as the housing, wherein the charging coil antenna is configured to receive a magnetic field to provide power to the pulse generator circuitry, and wherein the charging coil antenna is coupled by the electrical connections to other of the feedthrough pins in the first cavity.

7. The implantable pulse generator of claim 6, wherein power provided to the pulse generator circuitry by the charging coil antenna comprises power provided to the recharge the battery that provides power to the pulse generator circuitry.

8. The implantable pulse generator of claim 6, wherein the charging coil antenna encircles the housing.

9. The implantable pulse generator of claim 6, wherein the charging coil antenna does not overlap with the housing.

10. The implantable pulse generator of claim 6, further comprising an overmold encompassing at least a part of the housing and the charging coil antenna.

11. The implantable pulse generator of claim 1, further comprising a data antenna outside of the housing configured to receive and/or transmit data to an external controller, wherein the data antenna is coupled by the electrical connections to other of the feedthrough pins in the first cavity.

12. The implantable pulse generator of claim 11, wherein the housing is circular, and wherein the data antenna is curved to follow at least a portion a periphery of the housing.

13. The implantable pulse generator of claim 1, wherein the housing comprises a cylindrical portion configured to be recessed in a hole in a patient's skull.

14. The implantable pulse generator of claim 13, wherein the housing further comprises at least partial holes configured to accept bone screws to allow the implantable pulse generator to be affixed to a skull of a patient when the cylindrical portion of the housing is recessed in the hole in the patient's skull.

15. The implantable pulse generator of claim 1, wherein the at least one electrode wire cable is flexible.

16. The implantable pulse generator of claim 1, wherein there are two electrode wire cables and two connector blocks.

* * * * *